US009835705B2

(12) United States Patent
Weingartner et al.

(10) Patent No.: US 9,835,705 B2
(45) Date of Patent: Dec. 5, 2017

(54) SYSTEM AND METHOD FOR FREE-BREATHING VOLUMETRIC IMAGING OF CARDIAC TISSUE

(71) Applicants: Sebastian Weingartner, Heidelberg (DE); Mehmet Akcakaya, Cambridge, MA (US); Reza Nezafat, Newton, MA (US)

(72) Inventors: Sebastian Weingartner, Heidelberg (DE); Mehmet Akcakaya, Cambridge, MA (US); Reza Nezafat, Newton, MA (US)

(73) Assignee: Beth Israel Deaconess Medical Center, Inc., Boston, MA (US)

( * ) Notice: Subject to any disclaimer, the term of this patent is extended or adjusted under 35 U.S.C. 154(b) by 600 days.

(21) Appl. No.: 14/536,008

(22) Filed: Nov. 7, 2014

(65) Prior Publication Data

US 2015/0123659 A1    May 7, 2015

Related U.S. Application Data

(60) Provisional application No. 61/901,168, filed on Nov. 7, 2013.

(51) Int. Cl.
*G01V 3/00* (2006.01)
*G01R 33/50* (2006.01)
(Continued)

(52) U.S. Cl.
CPC .............. *G01R 33/50* (2013.01); *A61B 5/055* (2013.01); *A61B 5/7285* (2013.01); *G01R 33/5602* (2013.01); *A61B 2576/023* (2013.01); *G01R 33/4818* (2013.01); *G01R 33/4822* (2013.01); *G01R 33/5613* (2013.01); *G01R 33/5673* (2013.01); *G01R 33/5676* (2013.01); *G01R 33/56325* (2013.01); *G01R 33/56509* (2013.01)

(58) Field of Classification Search
USPC ........................................................ 324/309
See application file for complete search history.

(56) References Cited

U.S. PATENT DOCUMENTS 6,078,175 A * 6/2000 Foo .................. G01R 33/56341
                                                                324/300
6,144,200 A * 11/2000 Epstein .............. G01R 33/5615
                                                                324/306

(Continued)

*Primary Examiner* — Rodney Fuller
(74) *Attorney, Agent, or Firm* — Quarles & Brady LLP

(57) ABSTRACT

A magnetic resonance imaging (MRI) system and methods are provided for producing images of a subject. In some aspects, a method includes identifying a point in the cardiac cycle, performing an inversion recovery (IR) pulse at a selected time point from the pre-determined point, and sampling a k-space segment at an inversion time from the IR pulse that is substantially coincident with the pre-determined point. The method also includes repeating the IR pulse and k-space sampling for multiple inversion times, and multiple segments of k-space, in an interleaved manner, to generate datasets having T1-weighted contrasts determined by their respective inversion times. The method further includes reconstructing three-dimensional (3D) spatially-aligned images using the datasets, and generating a T1 recovery map by combining the 3D images. In some aspects, a prospective/retrospective scheme may be used to obtain data fully sampled in the center of k-space and randomly undersampled in the outer regions.

14 Claims, 10 Drawing Sheets

(51) Int. Cl.

| | | |
|---|---|---|
| *A61B 5/055* | (2006.01) | |
| *G01R 33/56* | (2006.01) | |
| *A61B 5/00* | (2006.01) | |
| G01R 33/48 | (2006.01) | |
| G01R 33/561 | (2006.01) | |
| G01R 33/563 | (2006.01) | |
| G01R 33/565 | (2006.01) | |
| G01R 33/567 | (2006.01) | |

(56) References Cited

U.S. PATENT DOCUMENTS

| | | | | |
|---|---|---|---|---|
| 2002/0077538 | A1* | 6/2002 | Saranathan | G01R 33/567 600/410 |
| 2004/0155653 | A1* | 8/2004 | Larson | G01R 33/5676 324/309 |
| 2005/0245812 | A1* | 11/2005 | Kim | A61B 5/055 600/410 |
| 2009/0212773 | A1* | 8/2009 | Feinberg | G01R 33/4818 324/309 |
| 2010/0222666 | A1* | 9/2010 | Foo | A61B 5/055 600/413 |
| 2012/0257806 | A1* | 10/2012 | Sheltraw | A61B 5/055 382/131 |
| 2013/0251225 | A1* | 9/2013 | Liu | G01R 33/5673 382/131 |
| 2014/0037171 | A1* | 2/2014 | Bhat | G06T 11/003 382/131 |
| 2016/0003928 | A1* | 1/2016 | Chen | G01R 33/5611 324/309 |
| 2016/0266223 | A1* | 9/2016 | Bi | A61B 5/02007 |

* cited by examiner

SYSTEM AND METHOD FOR FREE-BREATHING VOLUMETRIC IMAGING OF CARDIAC TISSUE

CROSS-REFERENCE TO RELATED APPLICATIONS

This application is based on, claims priority to, and incorporates here by reference in its entirety U.S. Provisional Application Ser. No. 61/901,168, filed Nov. 7, 2013, and entitled "SYSTEM AND METHOD FOR FREE-BREATHING VOLUMETRIC IMAGING OF CARDIAC TISSUE."

STATEMENT REGARDING FEDERALLY SPONSORED RESEARCH

This invention was made with government support under R01EB008743-01A2 awarded by the National Institutes of Health. The government has certain rights in the invention.

BACKGROUND OF THE INVENTION

The field of the invention is systems and methods for magnetic resonance imaging (MRI). More particularly, the invention relates to systems and methods for high-resolution, volumetric MRI imaging during free-breathing.

When a substance such as human tissue is subjected to a uniform magnetic field (polarizing field $B_0$), the individual magnetic moments of the nuclear spins in the tissue attempt to align with this polarizing field, but precess about it in random order at their characteristic Larmor frequency. Usually the nuclear spins are comprised of hydrogen atoms, but other NMR active nuclei are occasionally used. A net magnetic moment $M_z$ is produced in the direction of the polarizing field, but the randomly oriented magnetic components in the perpendicular, or transverse, plane (x-y plane) cancel one another. If, however, the substance, or tissue, is subjected to a magnetic field (excitation field $B_1$; also referred to as the radiofrequency (RF) field) which is in the x-y plane and which is near the Larmor frequency, the net aligned moment, $M_z$, may be rotated, or "tipped" into the x-y plane to produce a net transverse magnetic moment $M_t$, which is rotating, or spinning, in the x-y plane at the Larmor frequency. The practical value of this phenomenon resides in the signal which is emitted by the excited spins after the excitation field $B_1$ is terminated. There are a wide variety of measurement sequences in which this nuclear magnetic resonance (NMR) phenomenon is exploited.

When utilizing these signals to produce images, magnetic field gradients ($G_x$, $G_y$, and $G_z$) are employed. Typically, the region to be imaged experiences a sequence of measurement cycles in which these gradients vary according to the particular localization method being used. The emitted MR signals are detected using a receiver coil. The MRI signals are then digitized and processed to reconstruct the image using one of many well-known reconstruction techniques.

To do so, the signals are often weighted in different ways to give preference to or consider different sub-signals or so-called contrast mechanisms. Two basic "contrast mechanisms" commonly utilized in MR imaging are the spin-lattice (or longitudinal or $T_1$) relaxation time or spin-spin (or transverse or $T_2$) relaxation time. However, there are a variety of other mechanisms for eliciting contrast in MRI, including $T_2^*$. Specifically, $T_2^*$ is a quantity related to $T_2$, but includes dephasing effects. That is, $T_2^*$ is a quantity related to spin-spin relaxation and, in addition, relating magnetic field inhomogeneities and susceptibility effects. Often, instead of $T_2^*$, these quantities are preferably expressed in terms of relaxation, or the inverse of the $T_2^*$ time constant, represented as $R_2^*$.

Focal myocardial scar due to ischemic or non-ischemic heart disease can be assessed using late gadolinium enhancement (LGE) on cardiac MR (CMR). This technique relies on differences in contrast washout between infarcted and healthy myocardium for visualization of necrotic tissue. However, LGE imaging cannot identify diffuse or interstitial myocardial fibrosis in patients with non-ischemic disease where the collagen deposition is commonly diffused across the myocardium and is not focal. Quantitative myocardial $T_1$ mapping is an emerging technique that allows assessment of diffuse fibrosis in the myocardium. The concentration of a gadolinium contrast agent is inversely proportional to the $T_1$ time. Hence, $T_1$ quantification allows inference on the extracellular volume of the myocardium and therefore provides a measurement for the collagen content. It has been shown that this enables both the identification of focal and diffuse fibrosis in the myocardium.

Quantitative $T_1$ mapping is commonly performed by acquiring a series of inversion-recovery images each acquired using different inversion times. The image intensities are then fit to a $T_1$ relaxation curve to estimate $T_1$ maps. The two dimensional (2D) Look-Locker imaging sequence is most commonly used for evaluation of myocardial $T_1$ times. In this technique, a series of $T_1$-weighted images is acquired after the application of a single inversion pulse. However, due to cardiac motion, different images are acquired at different heart phases allowing only regional-wise calculation of $T_1$. A Modified Look-Locker Inversion recovery sequence (MOLLI) attempted to address this limitation by employing image acquisition along with ECG triggering to a specific cardiac phase. However, a relatively long scan time was required to provide a sufficient sampling of the $T_1$ curve due to recovery periods of the longitudinal magnetization. A shortened MOLLI sequence was later proposed for acquisition myocardial $T_1$ maps in reduced scan times, where a gradual reduction of recovery periods was employed in combination with a conditional data-exclusion scheme to allow $T_1$ mapping in nine heart beats. In addition, an alternative way to overcome the problem of long recovery periods has been to employ saturation recovery, for example, using an ECG triggered Look-Locker approach, or repeat in every heart beat. However, all of the aforementioned methods employ 2D imaging during a single breath-hold per slice, with limited spatial resolution, coverage and signal-to-noise ratio (SNR).

Although three-dimensional (3D) imaging provides improved resolution, SNR and coverage, volumetric 3D $T_1$ mapping is very challenging due to long scan times and spatial misregistration induced by respiratory motion between the acquisitions of images with different inversion times. Some recent studies have reported use of 3D sequences for in-vivo myocardial $T_1$ mapping. For instance, in one approach, a variable flip angle $T_1$ mapping method for 3D imaging was implemented, wherein sets of successive images were acquired with different flip angles to generate varying $T_1$-weighted contrasts. For each image set, retrospective cardiac gating was then applied to obtain one image per heart-phase per flip-angle. In another approach, $T_1$ quantification was proposed using an interleaved acquisition of phase images in a phase-sensitive inversion recovery (PSIR) technique. Acquisition of one PSIR 3D volume was performed during prolonged breath-holds, limiting acquisition to roughly 24 seconds. In yet another approach, acquisition of two subsequent 3D inversion recovery images with different inversion times were used for $T_1$ quantification. Image acquisition was free-breathing, using navigator (NAV) triggering for respiratory motion compensation. However, these approaches used two separate imaging datasets for estimating the $T_1$ maps in order to shorten scan time and reduce spatial misregistration, which can adversely impact the accuracy of $T_1$ maps.

Therefore, given the drawbacks of previous approaches, there is a need for new magnetic resonance imaging techniques capable of providing accurate volumetric assessment of cardiac tissue, including evaluation of scar tissue and diffuse myocardial fibrosis. Specifically, new approaches are needed for generating high-quality, free-breathing post-contrast 3D $T_1$ maps.

SUMMARY OF THE INVENTION

The present invention overcomes the aforementioned drawbacks by providing a magnetic resonance imaging (MRI) system and methods for producing high-resolution, spatially-aligned images of a subject during free-breathing. Specifically, an approach is introduced for acquiring multiple segmented three-dimensional (3D) $T_1$-weighted inversion recovery images using a number of inversion times, in an interleaved manner. In some aspects, a mixed prospective/retrospective navigator scheme may be used to obtain the 3D k-space data that is fully sampled in the center of k-space and randomly undersampled in the outer regions of k-space. The resulting 3D k-space data may then be reconstructed, for example, using a compressed sensing technique and used to generate 3D $T_1$ maps that include compensation for respiratory motion.

In accordance with one aspect of the invention, a method for producing images of a subject using a magnetic resonance imaging (MRI) system is provided. The method includes identifying a pre-determined point in a cardiac cycle of a subject, performing with a MRI system an inversion recovery (IR) pulse at a selected one of a plurality of time points within the cardiac cycle of the subject, and sampling a segment of k-space with the MRI system at an inversion time from the IR pulse that is substantially coincident with the pre-determined point in the cardiac cycle. The method also includes repeating the IR pulse and k-space sampling for a plurality of inversion times to achieve a plurality of T1-weighted contrasts by performing the IR pulse at a different one of the plurality of time points from the selected one of the plurality of time points until an IR pulse has been performed at all of the plurality of time points. The method also includes performing above steps for each of a plurality of segments of k-space to generate datasets having T1-weighted contrasts determined by respective inversion times, and reconstructing a set of three-dimensional (3D) spatially-aligned images using the datasets. The method further includes generating a T1 recovery map by combining the set of the 3D spatially-aligned images.

In accordance with another aspect of the invention a magnetic resonance imaging (MRI) system is provided. The system includes a magnet system configured to generate a polarizing magnetic field about at least a portion of a subject arranged in the MRI system and a magnetic gradient system including a plurality of magnetic gradient coils configured to apply at least one magnetic gradient field to the polarizing magnetic field. The system also includes a radio frequency (RF) system configured to apply an RF field to the subject and to receive magnetic resonance signals therefrom. The system further includes a computer system programmed to identify a pre-determined point in a cardiac cycle of a subject and control the magnetic gradient system and the RF system according to a pulse sequence. The computer system is also programmed to perform an inversion recovery (IR) pulse at a selected one of a plurality of time points within the cardiac cycle of the subject and sample a segment of k-space at an inversion time from the IR pulse that is substantially coincident with the pre-determined point in the cardiac cycle. The computer system is also configured to repeat the IR pulse and k-space sampling for a plurality of inversion times to achieve a plurality of T1-weighted contrasts by performing the IR pulse at a different one of the plurality of time points from the selected one of the plurality of time points until an IR pulse has been performed at all of the plurality of time points. The computer system is further configured to perform above steps for each of a plurality of segments of k-space to generate datasets having T1-weighted contrasts determined by respective inversion times, and reconstruct a set of three-dimensional (3D) spatially-aligned images using the datasets. Finally, the computer system is configured to generate a T1 recovery map by combining the set of the 3D spatially-aligned images.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
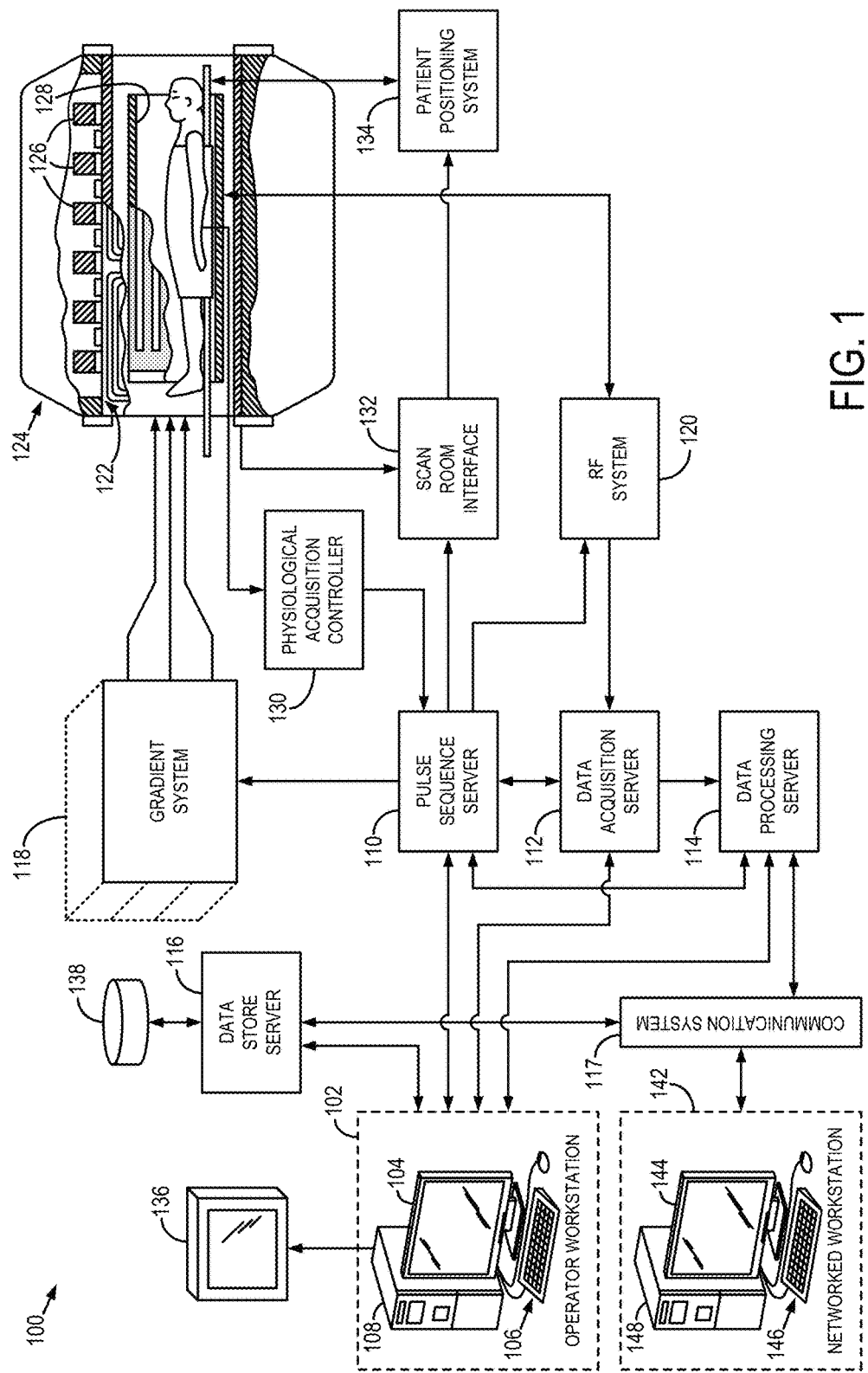
FIG. 1 is an example of a block diagram of an example magnetic resonance (MRI) system for use in accordance with the present disclosure.

The present disclosure provides a system and methods for volumetric quantification of $T_1$ relaxation times in an imaged subject. Specifically, an interleaved pulse sequence is introduced along with an acquisition approach suitable for use during free-breathing. In particular, the interleaved pulse sequence includes acquisition of multiple segments of inversion recovery images using multiple inversion times, in an interleaved fashion that ensures spatially-aligned images. As will become apparent, embodiments of the present disclosure may be advantageously applied to cardiac imaging, for example, to determine arrhythmias and disease, including facilitating assessment of scar and diffuse fibrosis.

In standard 2D $T_1$ mapping of cardiac tissue, spatial misalignment of the different $T_1$ weighted images can lead to image artifacts in sub-endocardium and sub-epicardium regions. Such artifacts due to breathing motion can significantly reduce the effective resolution of $T_1$ mapping. Typically, numerous breath-holds are required to provide full-heart coverage, at up to 17 seconds duration each. This demanding procedure can lower the effectiveness of the subject's breath-hold, inducing pronounced misalignment in the presence of incomplete breath-holds. As will be described, prominent differences can be observed between the maximum amounts of motion in the breath-hold approach compared to a free-breathing approach, indicating that there are slices with imperfect breath-holds. Moreover, long breath-holds are also known to suffer from a linear drift in foot-head direction, for example, on the order of 0.4 mm/second in the right diaphragm of a subject. In addition, rest periods necessary between subsequent breath-holds lead to prolonged scan times, For example, in the case of left ventricle (LV) coverage using a 2D multi-slice sequence, scan times may last up to 10 minutes.

Therefore, the system and methods provided by the present disclosure introduce an approach that may be used during free breathing. In particular, with respect to the interleaved pulse sequence and acquisition scheme described, although the acquisition window per cardiac cycle can be reduced for a 3D image acquisition, the overall scan time for the same volume during free-breathing can be substantially shortened as compared to a breath-held approach.

In some approaches, attempts for mitigating spatial misalignment of the images have included applying retrospective image registration techniques. However, compared to prospective image alignment, this data post-processing complicates image reconstruction, since image registration algorithms are sensitive to the applied similarity-measures and the regularization parameters, and require to compromise between accuracy, precision and reliability. In particular for the case of 2D imaging, the effectiveness of image registration algorithms is lowered by in-plane motion and the associated displacement of anatomical features.

In addition, 2D $T_1$ mapping methods, such as MOLLI or ShMOLLI, are acquired in a non-segmented, single-shot data acquisition process. Despite the application of acceleration techniques, long acquisition windows (around 200 ms) often exceed the duration of the mid-diastole quiescence. Therefore, cardiac motion artifacts could adversely impact the image and $T_1$ map quality. By contrast, the $T_1$ mapping scheme described herein utilizes a segmented data-acquisition, which enables the use of a subject-specific acquisition window to reduce cardiac motion. Furthermore, the segmented data acquisition described herein allows for resolutions beyond single-shot imaging, potentially providing improved localization of abnormal $T_1$ times and reduced partial-volume effects.

Referring now particularly to FIG. 1, an example of a magnetic resonance imaging (MRI) system 100 is illustrated. The MRI system 100 includes an operator workstation 102, which will typically include a display 104, one or more input devices 106, such as a keyboard and mouse, and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to four servers: a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 117, which may include any suitable network connection, whether wired, wireless, or a combination of both. As an example, the communication system 117 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms necessary to perform the prescribed scan are produced and applied to the gradient system 118, which excites gradient coils in an assembly 122 to produce the magnetic field gradients and used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil (not shown in FIG. 1), are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays (not shown in FIG. 1).

The RF system 120 also includes one or more RF receiver channels. Each RF receiver channel includes an RF preamplifier that amplifies the magnetic resonance signal received by the coil 128 to which it is connected, and a detector that detects and digitizes the quadrature components of the received magnetic resonance signal. The magnitude of the received magnetic resonance signal may, therefore, be determined at any sampled point by the square root of the sum of the squares of the and components:

$$M = \sqrt{I^2 + Q^2}$$ Eqn. (1);

and the phase of the received magnetic resonance signal may also be determined according to the following relationship:

$$\varphi = \tan^{-1}\left(\frac{Q}{I}\right).$$ Eqn. (2)

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during pre-scans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled, as will be described. In still another example, the data acquisition server 112 may also be employed to process magnetic resonance signals used to detect the arrival of a contrast agent in a magnetic resonance angiography (MRA) scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction algorithms, such as iterative or backprojection reconstruction algorithms; applying filters to raw k-space data or to reconstructed images; generating functional magnetic resonance images; calculating motion or flow images; and so on.

Images reconstructed by the data processing server 114 are conveyed back to the operator workstation 102 where they are stored. Real-time images are stored in a data base memory cache (not shown in FIG. 1), from which they may be output to operator display 112 or a display 136 that is located near the magnet assembly 124 for use by attending physicians. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144; one or more input devices 146, such as a keyboard and mouse; and a processor 148. The networked workstation 142 may be located within the same facility as the operator workstation 102, or in a different facility, such as a different healthcare institution or clinic.

The networked workstation 142, whether within the same facility or in a different facility as the operator workstation 102, may gain remote access to the data processing server 114 or data store server 116 via the communication system 117. Accordingly, multiple networked workstations 142 may have access to the data processing server 114 and the data store server 116. In this manner, magnetic resonance data, reconstructed images, or other data may exchanged between the data processing server 114 or the data store server 116 and the networked workstations 142, such that the data or images may be remotely processed by a networked workstation 142. This data may be exchanged in any suitable format, such as in accordance with the transmission control protocol (TCP), the internet protocol (IP), or other known or suitable protocols.

Figure 2A:
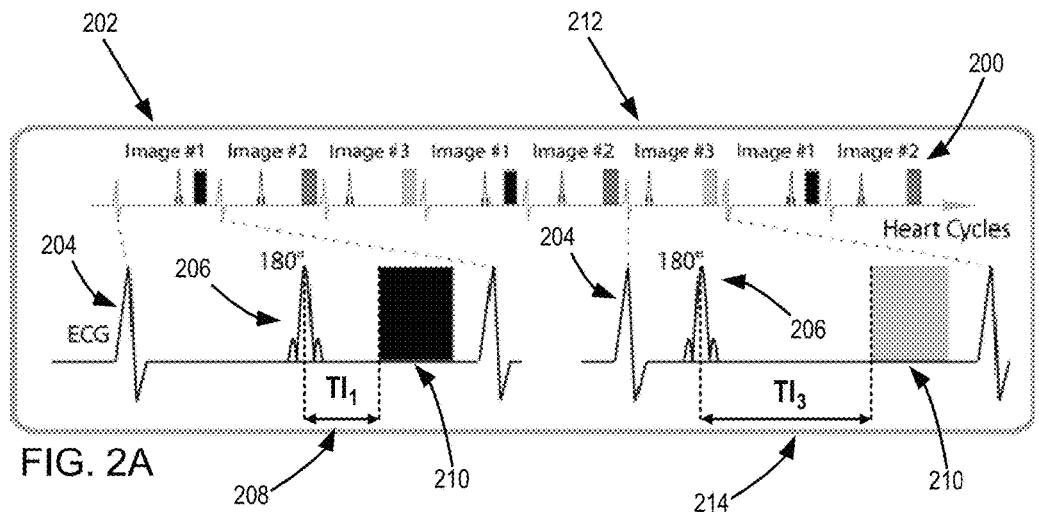
FIG. 2A is a graphic representation of a pulse sequence depicting the interleaved acquisition of multiple segmented inversion recovery (IR) images with different inversion times.

Turning to FIG. 2(a), a schematic diagram of an example pulse sequence 200, in accordance with aspects of the present disclosure, is shown. Pulse sequence 200 may played out using, for example, the above-described MRI system 100, or any suitable MRI system, in order to acquire spatially-aligned images for generating accurate 3D $T_1$ recovery maps with sufficient anatomical coverage. In some aspects, pulse sequence 200 may be applied following administration of a contrast agent to a subject and directed, but not limited, to cardiac applications.

As illustrated in FIG. 2(a), pulse sequence 200 may include multiple pulse modules configured to acquire, in an interleaved manner, multiple inversion recovery k-space data segments associated with various images. Particularly with reference to a representative pulse module 202, acquisition of a segment of k-space may begin with obtaining a trigger 204, identifying point(s) in a cardiac cycle of a subject. For example, the trigger 204 can be based on electrocardiogram (ECG) measurements, although other approaches that provide information related to a subject's cardiac cycle may also be possible. After a delay period ("trigger delay") elapses from the trigger 204, an inverting excitation pulse 206 is then applied, wherein the inverting excitation pulse 206 is substantially equal to 180°, and can include a two-dimensional (2D) or preferably three-dimensional (3D) excitation.

The inverting excitation pulse 206 is then be followed by an inverting time ($TI_1$) 208 delay prior to readout via a data sampling pulse sequence 210. In some aspects, a balanced steady state free precession (bSSFP) sequence may be utilized for the data sampling pulse sequence 210, although other acquisition methods may also be possible. For instance, a TR/TE=2.6 ms/1.0 ms, flip angle=35°, resolution=1.7×2.1×10 mm$^3$, FOV=300×300×100 mm$^3$ may be utilized, although one skilled in the art would readily appreciate that any suitable variations may also be possible, and considered within the scope of the present disclosure.

As shown in FIG. 2(a), pulse sequence 200 can include multiple pulse modules similar to pulse module 202, which may include different inverting times. For example, another representative pulse module 212 may begin by applying an inverting excitation pulse 206 following trigger 204, as described. However, in this pulse module 212, the inversion time ($TI_3$) 214 delay between the inverting excitation pulse 206 and data sampling pulse sequence 210 is different in comparison to the above-described pulse module 202. That is, the inverting excitation pulse 206 occurs at a different temporal location relative to the trigger 204 when compared to the position of the inverting excitation pulse 206 of pulse module 202.

By way of example, pulse sequence 200 can include pulse modules having anywhere between 3 to 8 different inversion times, although other values may also be possible. For simplicity, selected inversion times of the different interleaves can be linearly distributed, spanning over a range of inversion times, such as 100 to 700 ms. However, it is envisioned that selected inversion times need not be linearly distributed, and a comprehensive evaluation of the optimal inversion time distribution may improve the accuracy of $T_1$ fitting process, as described below, and thus further improve estimation of the $T_1$ maps.

Multiple datasets corresponding to respective k-space segments for different images may be acquired in an interleaved manner, as illustrated in FIG. 2(a). In some aspects, acquired 3D k-space datasets may be fully sampled in the central region of k-space and randomly undersampled in outer region of k-space. The acquired datasets, may then be used in a suitable reconstruction process to obtain a number of spatially-aligned images, the images having various contrasts in dependence of the amount of signal recovery via selected inversion times. For example, 3D k-space datasets may be reconstructed using a compressed sensing technique, such as low-dimensional structure self-learning and thresholding technique. This approach provides an improved reconstruction algorithm particularly with respect cardiac applications, where patient- and anatomy-specific sparsifying transforms may be generated from central k-space low resolution data, which may then be iteratively refined.

Figure 2B:
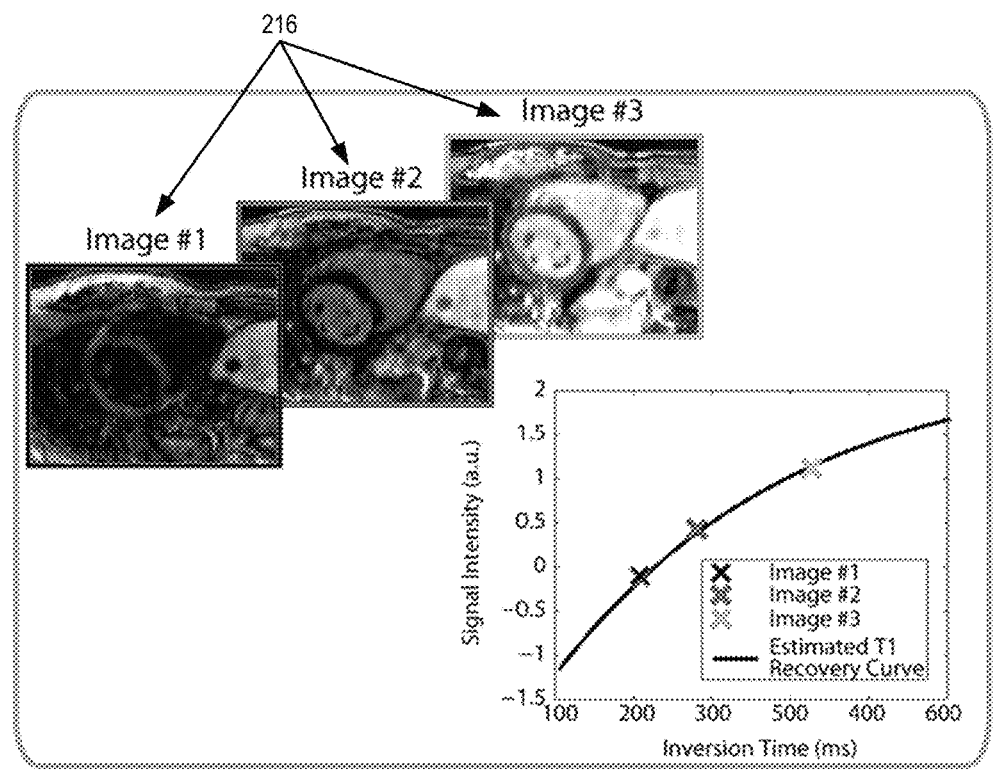
FIG. 2B is graphic representation of examples of spatially-aligned images used to generate $T_1$ maps accordance with the present disclosure.

With reference to FIG. 2(b), a non-limiting example is shown, illustrating how spatially-aligned images 216, acquired using three different inversion times, in a manner described, may used to generate $T_1$ maps. In particular, a pixel-wise or voxel-wise analysis of signal intensities corresponding to the spatially aligned images 216 may be performed. That is, signal intensities of corresponding pixels or voxels on the images may be utilized in a fitting process aimed at directly extracting $T_1$ values. In some aspects, the fit may be performed by applying the following two-parameter model to the image intensities:

$$S(T_{inv};M_0,T_1)=M_0(1-2e^{-T_{inv}/T_1}) \qquad (1);$$

where $M_0$ is the spin density and $T_1$ is the longitudinal relaxation time. A $T_1$ map may then be generated by extracting $T_1$ values for all desired pixels or voxels in the acquired images.

In the above-described pulse sequence 200, the magnetization preparation and the image data readout are advantageously applied within one heart-cycle. This inherently leaves the range of applicable inversion times to roughly 100-700 ms. For estimation of longer $T_1$ times, this may lead to an insufficient fit conditioning. Hence, it may be appreciated that the data acquisition approach presented above could be more suitable for applications related to post-contrast $T_1$ mapping.

Specifically, it is noted that, since the time between two inversion pulses may be less than the duration of one heart-cycle, a full recovery of the longitudinal relaxation curve after a previous magnetization preparation may not be achieved. As such, the resulting steady state of the longitudinal relaxation may deviate from the theoretical model of Eqn. 1. This may lead to a corruption of the determined $T_1$ times. Hence, in order to reduce the deviation of the steady-state from the theoretical model, the spread of the effective inversion times may be advantageously kept to approximately 100 to 600 ms to mitigate the problem of the insufficient recovery, since post-contrast $T_1$ times are typically in a range of 100-400 ms. In addition, addressing systematic deviations in the $T_1$ estimation described may include removing bias through a retrospective correction of the $T_1$ times using a calibration from phantom measurements.

In accordance with some aspects of the disclosure, image data, generated using pulse sequence 200 as described with respect to FIG. 2(a), may include compensation for respiratory motion. That is, the present disclosure recognizes that NAV-based gating and/or prospective slice tracking along with judicious k-space sampling scheme may be utilized to acquire image data during free-breathing, the data having the same general signal recovery necessary to obtain accurate 3D $T_1$ mapping. Therefore, along with the acquisition of k-space segments, a motion-tracking signal, such as a NAV-based motion-tracking signal, may be acquired. It is noted that other motion-tracking signals, such as bellows signals and the like, may be used instead of or in addition to a NAV-based motion-tracking signal.

As will be described, the motion-tracking signal may be compared against one or more selected threshold values to prospectively determine retention, rejection, and/or repetition of acquired datasets. In some aspects, threshold values may be pre-selected, or determined, say by monitoring the motion-tracking signal, in a manner that defines an acceptable amount of motion for the particular k-space segment(s) being acquired. In addition, differing threshold values may be used during acquisition of different regions of k-space.

In some aspects, reacquisition of all central k-space segments may be advantageously performed for all, many or most images, in the instance that the motion-tracking signal falls outside a selected or determined thresholds, or a threshold range, due to, say, respiratory motion. This would guarantee the same signal recovery throughout acquisition of each segment. However, only one instance of a k-space segment need be used in case of multiple accepted acquisitions of the same k-space segment for a given image. On the other hand, acquisition of datasets representing k-space segments in the outer k-space regions need not be repeated if the motion-tracking signal falls outside selected thresholds, and may be retrospectively identified and discarded. In this manner, 3D k-space datasets would be fully sampled in the central k-space and randomly undersampled in the outer region of k-space.

Figure 3:
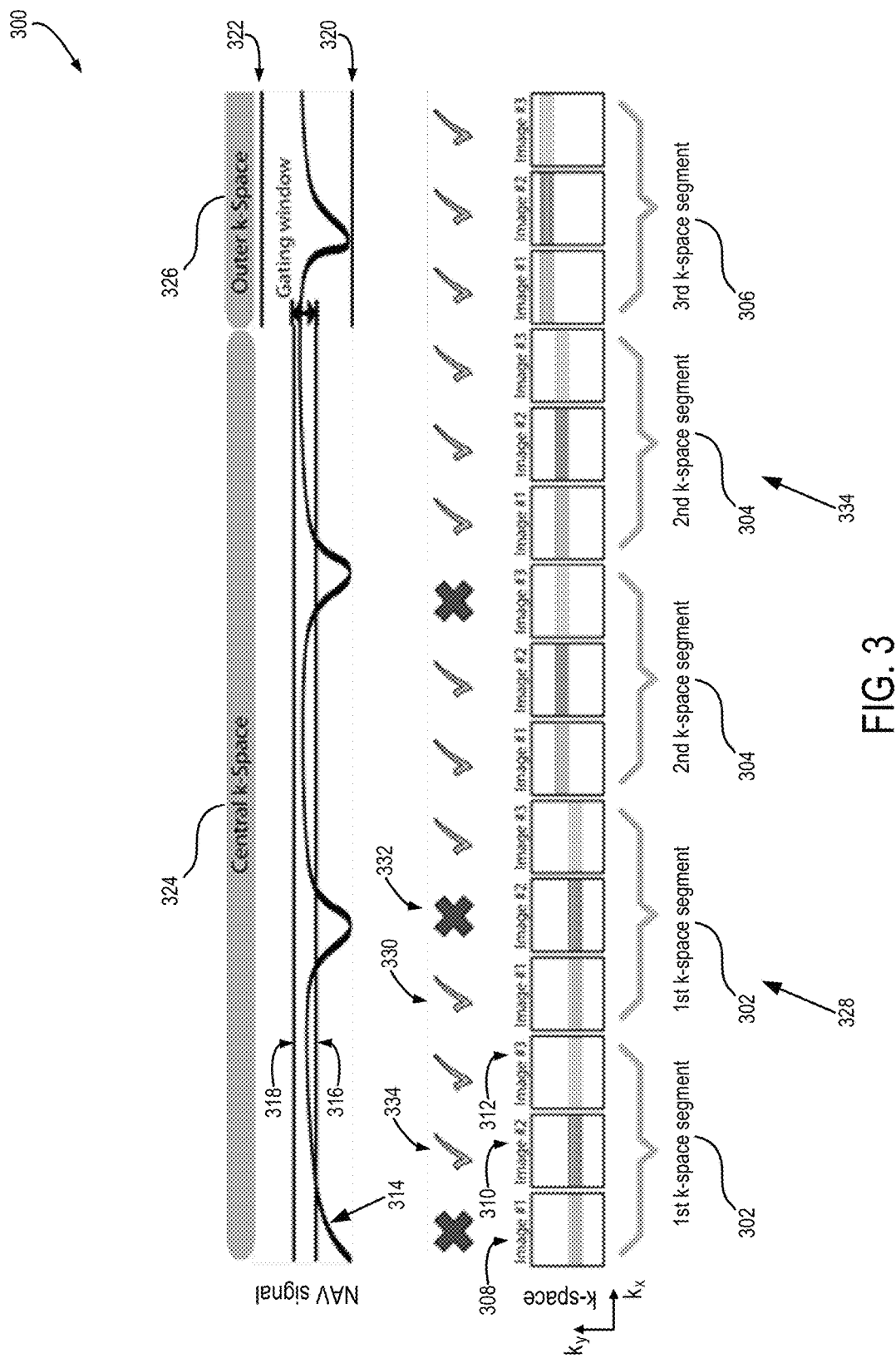
FIG. 3 is schematic representation illustrating an example of a prospective gating scheme for the central and outer regions of k-space in accordance with the present disclosure.

With reference to FIG. 3, a schematic for an example data sampling scheme 300 that includes protections against motion artifacts, is illustrated. Specifically, sampling scheme 300 shows interleaved acquisition of a number of k-space segments corresponding to a number of images in an image set. As described, such images can include different $T_1$ contrast weightings, for use in generating accurate 3D $T_1$ mapping. For simplicity, in the example sampling scheme 300 of FIG. 3, acquisition of datasets corresponding to Cartesian k-space segments, including a 1st k-space segment 302, a 2nd k-space segment 304, and a third k-space segment 306, is shown for a set of three images, which includes image #1 308, image #2 310, and image #3 312. However, one skilled in the art would readily recognize that such example is not limiting, and a sampling sequence could include any number of images and k-space segments, including non-Cartesian and 3D k-space segments, and be considered within the scope of the present disclosure.

As shown in FIG. 3, threshold values 316, 318, 320 and 322 identify minimum and maximum acceptable values, respectively, for a motion-tracking signal 314. Specifically, in accordance with aspects of the present disclosure, threshold values 316, 318 correspond to the center region of k-space 324, while threshold values 320 and 322 correspond to the outer region of k-space 326. By way of example, threshold values 316 and 318 may be selected to implement, say, a 7 mm gating window, while threshold values 320, 322 may be selected to define a gating window that is substantially more relaxed and/or non-existent.

During acquisition of the k-space segments, the motion-tracking signal 314 is acquired and compared against the one or more threshold values 304, 306 and 308, 310. In this regard, the present invention is configured to determine in real time or substantially real time, whether a particular k-space segment for a particular image was acquired during motion. In the illustrated example, the 1st k-space segment 302 for image #1 308 occurs during undesired motion, as indicated by the motion-tracking signal 314 being below the lower threshold value 316 during the acquisition of the 1st k-space segment 302 for image #1 308. As such, the acquisition is readily adjusted to repeat the acquisition of the 1st k-space segment 302, as generally indicated at 328. Upon repetition of the acquisition, there is no undesired motion during the acquisition of the 1st k-space segment 302 for image #1 308, as indicated at 330. However, there is undesired motion during the during the acquisition of the 1st k-space segment 302 for image #2 310, as indicated at 332. However, as the data required for the 1st k-space segment 302 for image #2 310 was already acquired during the prior repetition 334, there is no need to repeat the acquisition of the 1st k-space segment 302 for the entire image set in order to obtain the 1st k-space segment 302 for image #2 310. Similarly, the same issue and solution is illustrated relative to the first acquisition of the 2nd k-space segment 304 for image #3 312. As such, a second acquisition of the 2nd k-space segment 328 for each image in the image set is performed, as indicated by 334.

With respect to the 3rd k-space segment 306 associated with the outer k-space 326 region, acquisition need not be repeated in the example shown, by virtue of the large gating window provided by threshold values 320 and 322. However, it is contemplated that in some instances the motion-tracking signal 314 values may fall outside the range determined by threshold values 320 and 322, a case in which reacquisition may be repeated. In addition, as described, acquisitions experiencing excessive motion may be retrospectively removed. In this manner, 3D k-space datasets may be acquired which are fully sampled in the central k-space region and randomly undersampled in the outer region of the k-space.

The actual magnetization signal is highly dependent on the magnetization history and consequently highly dependent on the order of the applied inversion times. To minimize the corruption introduced by insufficient recovery, it may be appreciated that the same recovery scheme be maintained for the central k-space and the outer k-space. Therefore, in some aspects, dummy interleaves may be acquired] for the repeated acquisitions of a k-space segment in the central k-space, even after data for the respective interleaf was already NAV-accepted.

Figure 4:
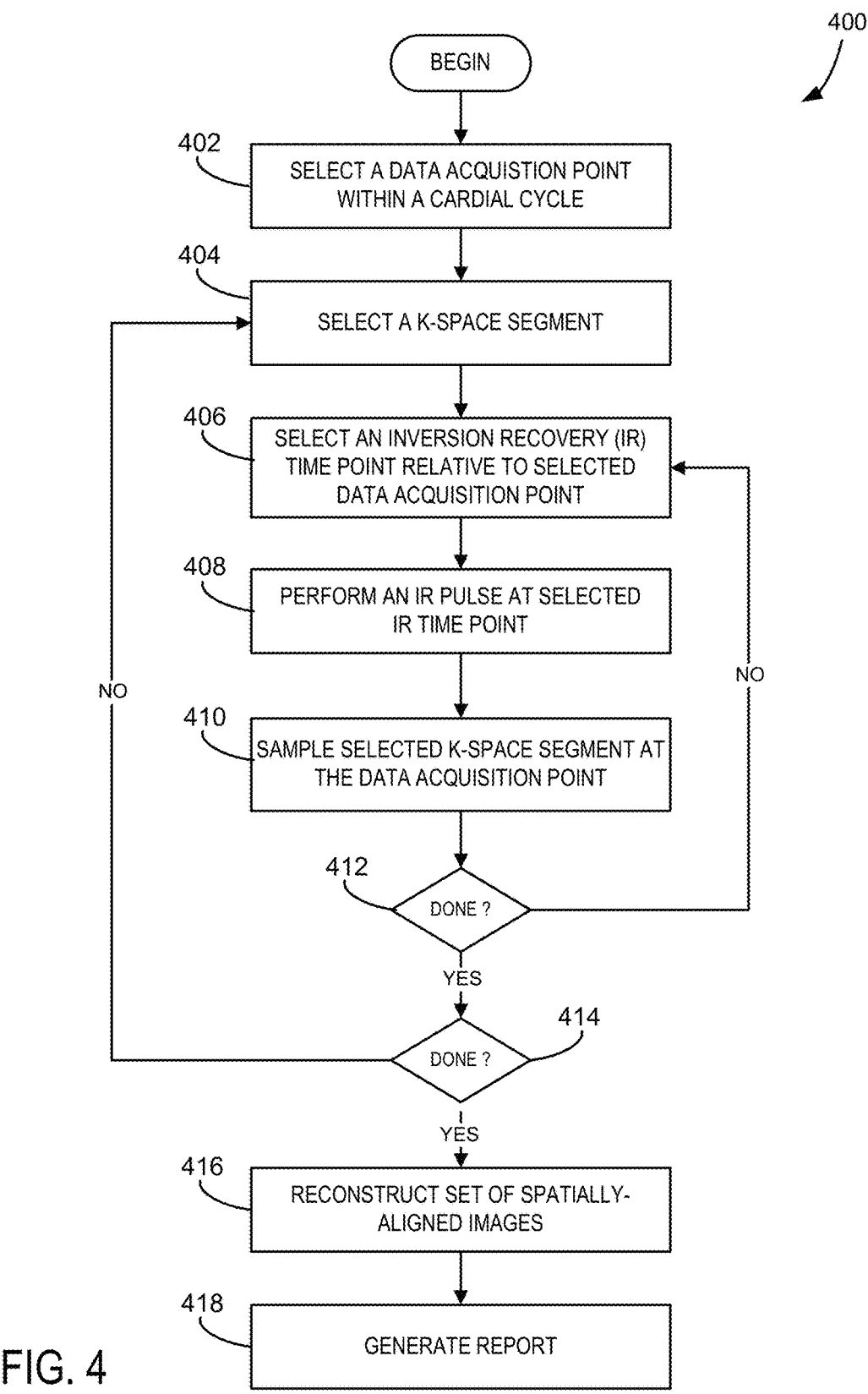
FIG. 4 shows steps of a process for an interleaved data acquisition, in accordance with aspects of the present disclosure.

Referring now to FIG. 4, steps of a process 400 for an interleaved data acquisition, in accordance with aspects of the present disclosure, are shown. Specifically, process 400 may begin with process block 402, whereby a data acquisition point within the cardiac cycle of a subject is selected, for example, from points identified using a cardiac tracking signal. In some aspects, such selection may be dependent on the duration of the data sampling pulse sequence utilized, and/or the inversion times necessary to obtain desirable $T_1$ contrast weightings. At process block 404 a k-space segment first is selected for data acquisition, as described, followed by selection of a first inversion recovery time point relative to the selected data acquisition point, as indicated by process block 406. At process block 408, an inversion recovery (IR) pulse may be performed at the first selected inversion recovery time point, followed by a sampling of the selected k-space segment at a pre-determined time point, or data acquisition time point from process block 410. As indicated by decision block 412, process blocks 406-410 may be repeated a number of times, in dependence of the desired number of $T_1$ contrast weightings. That is, an IR pulse may be performed at a different time point from the selected data acquisition point, or using different inversion times, followed by sampling of the selected k-space segment at the selected data acquisition point. Such process is repeated until all $T_1$ contrast weightings for the selected k-space segment have been acquired. Then, as indicated by decision block 414, process blocks 404-410 may be further repeated, in the manner described, for a number of iterations in dependence of the number of desired k-pace segments to generate multiple datasets having different T1-weighted contrasts determined by respective inversion times.

At process block 416 the acquired datasets may be used in a reconstruction process to obtain a set of three-dimensional (3D) spatially-aligned images. As described, reconstruction may be performed using a compressed sensing technique, such as low-dimensional structure self-learning and thresholding technique. Then at process block 418, a report may be generated of any form. In particular, the report may include generating a $T_1$ recovery map by combining the set of the 3D spatially-aligned images, for example, using a fitting process as described above.

Figure 5:
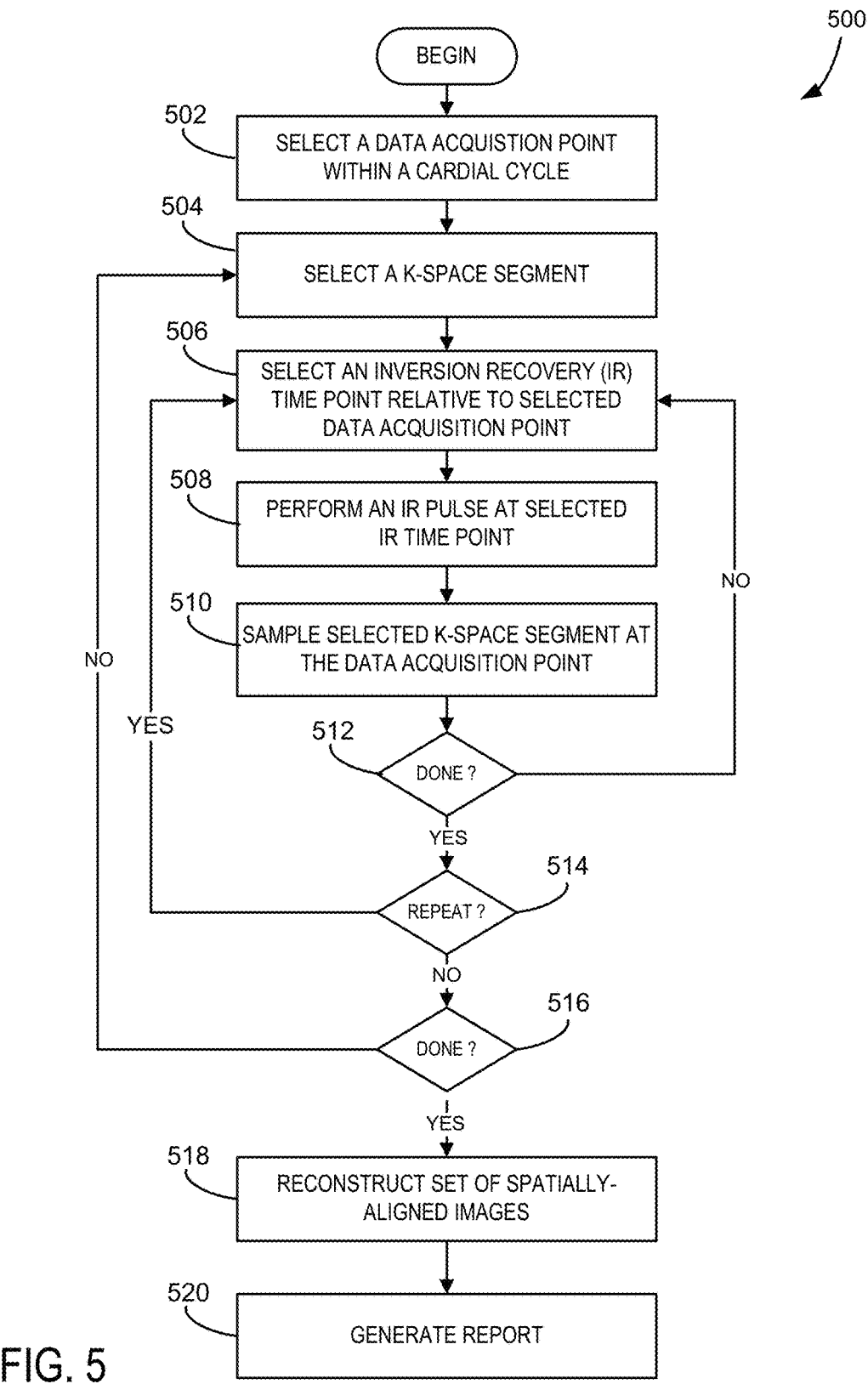
FIG. 5 shows steps of another process for an interleaved data acquisition, in accordance with aspects of the present disclosure.

Referring now to FIG. 5, steps of another process 500 for an interleaved data acquisition, in accordance with aspects of the present disclosure, are shown. In a manner similar to process 400 of FIG. 4, process 500 includes an interleaved acquisition of a multiple k-space segments using a number of inversion times following the inversion recovery pulses, and reconstruction a set of spatially-aligned images for use in generating and reporting $T_1$ recovery maps, as indicated by process blocks 502-520.

In addition, process 500 includes compensation for respiratory motion. That is, as indicated by decision block 514, datasets where a tracked motion signal has exceeded acceptable thresholds, as detailed in the example with reference to FIG. 3, may be prospectively reacquired or retrospectively discarded. In some aspects, acquisition of a selected k-space segment that corresponds to a center of k-space may be repeated by repeating process blocks 506-512, while datasets corresponding to a selected k-space segment corresponding to the outer k-space regions may be discarded during the reconstruction step of process block 518.

Specific examples are provided below, wherein an approach for assessing of diffuse myocardial fibrosis using a free-breathing 3D $T_1$ mapping method is presented. These examples are offered for illustrative purposes only, and is not intended to limit the scope of the present invention in any way. Indeed, various modifications of the invention in addition to those shown and described herein will become apparent to those skilled in the art from the foregoing description and the following example and fall within the scope of the appended claims. For example, specific examples for acquisition of interleaved 3D data based on ECG triggering and a compressed sensing image reconstruction are provided, although it will be appreciated that parameters and steps, as recited, may be altered or varied while still considered within the breadth and scope of the present invention. For example pulse duration, timing, amplitude, repetition, flip angle and so forth, and combinations thereof, as well as other image reconstruction approaches, are possible.

EXAMPLES

All studies were carried out on a 1.5T Philips Achieva (Philips, Best, The Netherlands) system using a 32-channel cardiac coil array. Data analysis of $T_1$ measurements was performed, wherein regions of interest (ROI) were manually drawn in the $T_1$ maps for quantitative assessment of the $T_1$ times and homogeneity in the myocardium, the left and right ventricle. The homogeneity of the estimated $T_1$ was assessed as the standard deviation within an ROI. A paired Student's t-test was used for assessment of statistical significance of the difference between the average estimated $T_1$ times in the myocardium and the homogeneity within the blood pools, where a P-value of <0.05 was considered to be significant.

To examine the spatial alignment of the images with different inversion times, five images per slice were selected for further analysis (all inversion times for the 3D sequence and the images 2, 4, 6, 8 and 10 for MOLLI). A software tool was developed in Matlab (The Math Works, Natick, Mass.) to manually draw closed contours around the left ventricle (LV) in each image separately. The LV center point was estimated as the centroid of this contour for each inversion time. For each slice the distance between the estimated center point in two successive images with different inversion times was assessed. This results in one motion quantification for each slice. The spatial registration in the entire dataset was represented by the average, the minimum and the maximum of this estimation among the slices of a dataset.

The higher SNR of the 3D T1 mapping approach of the present invention, compared to 2D imaging, beneficially affects the $T_1$ fit and the quality of the $T_1$ maps due to the increased excitation volume. This enables a reduction of the number of $T_1$-weighted images, which are required for a reliable $T_1$ map. By way of example, five different inversion times were chosen empirically as a trade-off between $T_1$ map quality and scan time.

Phantom Imaging

A phantom experiment was performed to examine the accuracy of the proposed 3D $T_1$ mapping sequence and confirm the consistency of the $T_1$ estimation along the slice encoding dimension. The phantom consisted of a bottle filled with water, copper-sulfate and sodium-chloride and a number of vials containing different liquids, with $T_1$ values ranging from approximately 200 to 500 ms.

The phantom was imaged using a 3D $T_1$ mapping method as described by in the present disclosure, along with a multi-slice 2D MOLLI and a 2D inversion recovery spin-echo sequence. The 3D $T_1$ mapping sequence used a balanced steady state free precession imaging readout (TR/TE=2.6 ms/1.0 ms, flip angle=35°, resolution=1.7×2.1×10 mm³, FOV=300×300×100 mm³) and was performed multiple times with 3 to 8 inversion times. For MOLLI the 3-3-5 scheme with optimized parameter values (TR/TE=2.6 ms/1.0 ms, flip angle=35°, in-plane resolution=1.7×2.1×10 mm³, slice-thickness=10 mm, FOV=300×300 mm²) was used and the $T_1$ maps were generated using exponential fitting with maximum likelihood estimation (MLE) and a flip angle independent correction of the measured $T_1$ value. For reference, an inversion-recovery spin-echo sequence was performed using the following parameters: TR/TE=15 s/10 ms, flip angle=90°, inversion times: 50, 100, 200, 400, 800, 1600 ms, scan time=6 hours. All scans were performed using a simulated ECG with a heart rate of 60 bpm. The average $T_1$ estimation for each phantom-compartment was compared between the different sequences. Since the $T_1$ values are nominally homogenous in each phantom compartment, as assessed by verification of manually drawn regions-of-interest (ROI), standard deviation was used as a measurement for signal homogeneity.

Figures 6A, 6B:
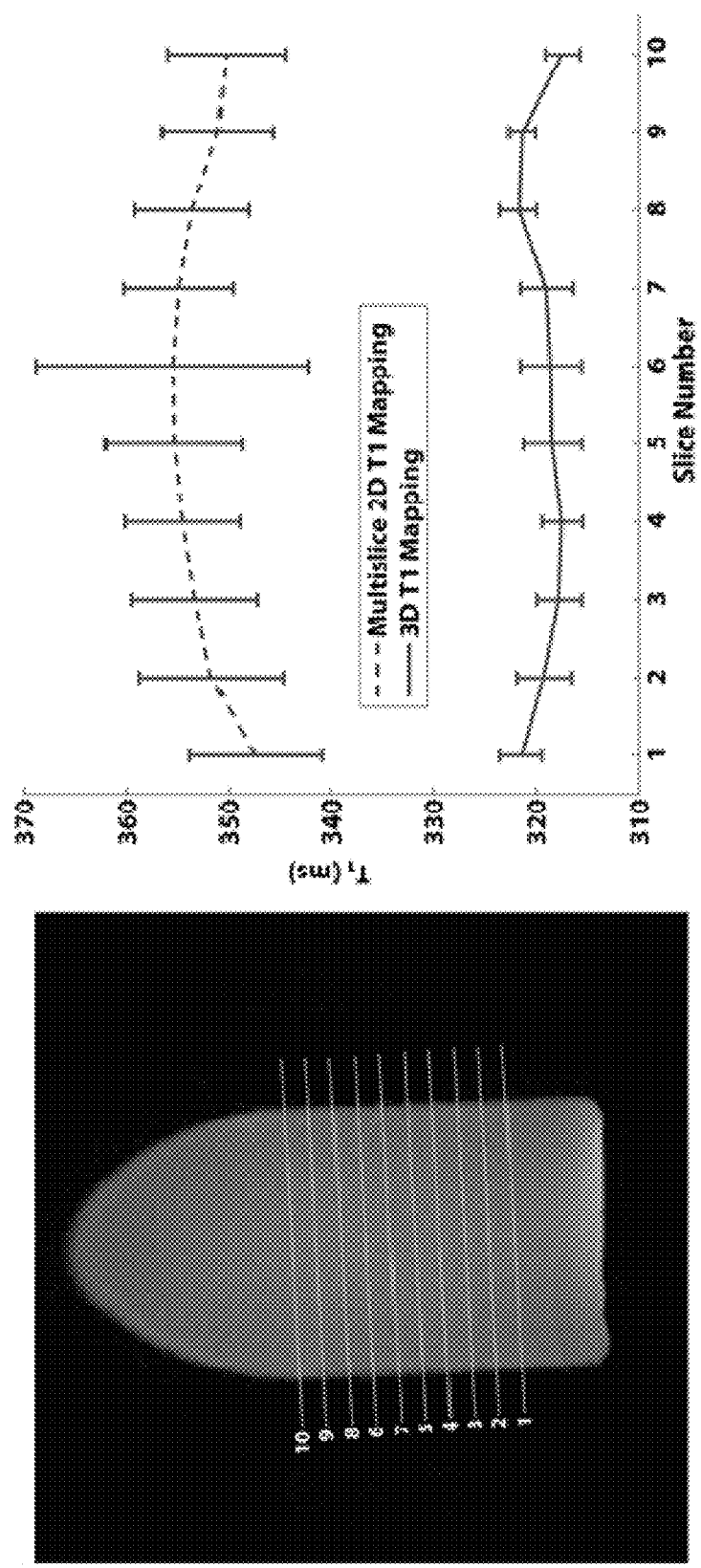
FIG. 6A is an image showing a phantom containing a homogeneous liquid with approximate slice locations.
FIG. 6B is a plot comparing $T_1$ times versus slice number for the bottle phantom of FIG. 6A along the slice encoding dimension using a 2D multi-slice technique and 3D $T_1$ mapping technique in accordance with the present disclosure.

Table 1 shows $T_1$ times determined with the 3D $T_1$ mapping sequence, MOLLI and the inversion recovery spin-echo sequence in phantom. Both MOLLI and the 3D sequences resulted in $T_1$ values close to the calculated $T_1$ from the spin-echo sequence, but with a relative difference of 0.5-11% and 7-12%, respectively. In addition, the standard deviation of the assessed $T_1$ times within the phantom compartments was significantly reduced for the 3D sequence compared to 2D MOLLI sequence (P<0.03). This is further illustrated in FIG. 6, which shows $T_1$ time measurements along the slice-encoding dimension. Variation in the $T_1$ time estimates across the slices is within the range of the in-slice variation.

TABLE 1

$T_1$ time phantom measurements comparing the 3D $T_1$ sequence of the present invention with a 2D MOLLI and a 2D spin echo sequence.

| | $T_1$ (ms) | | |
|---|---|---|---|
| 2D spin echo | 193 ± 0.6 | 308 ± 0.9 | 418 ± 2.6 |
| 2D MOLLI | 217 ± 7.3 | 330 ± 9.9 | 452 ± 9.3 |
| 3D $T_1$ mapping | 213 ± 2.1 | 311 ± 1.0 | 384 ± 1.7 |

In-Vivo Studies

In a prospective study, 9 healthy adult subjects (4 male, age 34.3±17.2 years) and 3 subjects with suspected cardiac disease (1 male, age 62.3±8.33 years) were recruited to undergo clinical CMR exams. All subjects were imaged using both the 3D $T_1$ mapping and multi-slice MOLLI sequences, in random order, 5 to 15 minutes after administration of 0.2 mmol/kg gadobenate dimeglumine (MultiHance, Bracco SpA, Milano, Italy). The 3D $T_1$ mapping sequence consisted of 5 imaging datasets acquired using different inversion times. Images with equal spatial resolution to MOLLI were acquired with the following sequence parameters: TR/TE=2.6 ms/1.0 ms, flip angle=35°, resolution=1.7×2.1×10 mm$^3$, FOV=300×300×100 mm$^3$, resulting in a nominal scan time of 3:10 min at a heart rate of 60 bpm and 100% gating efficiency for the acquisition of the central k-space. In addition, to demonstrate the feasibility of an improved spatial resolution, high resolution maps were acquired in five subjects with a resolution of 1.7×1.7×4 mm$^3$, a FOV of 300×300×100 mm$^3$ (TR/TE=3.0 ms/1.3 ms) and a nominal scan time of 9 minutes at 60 bpm and 100% efficiency.

Figure 7:
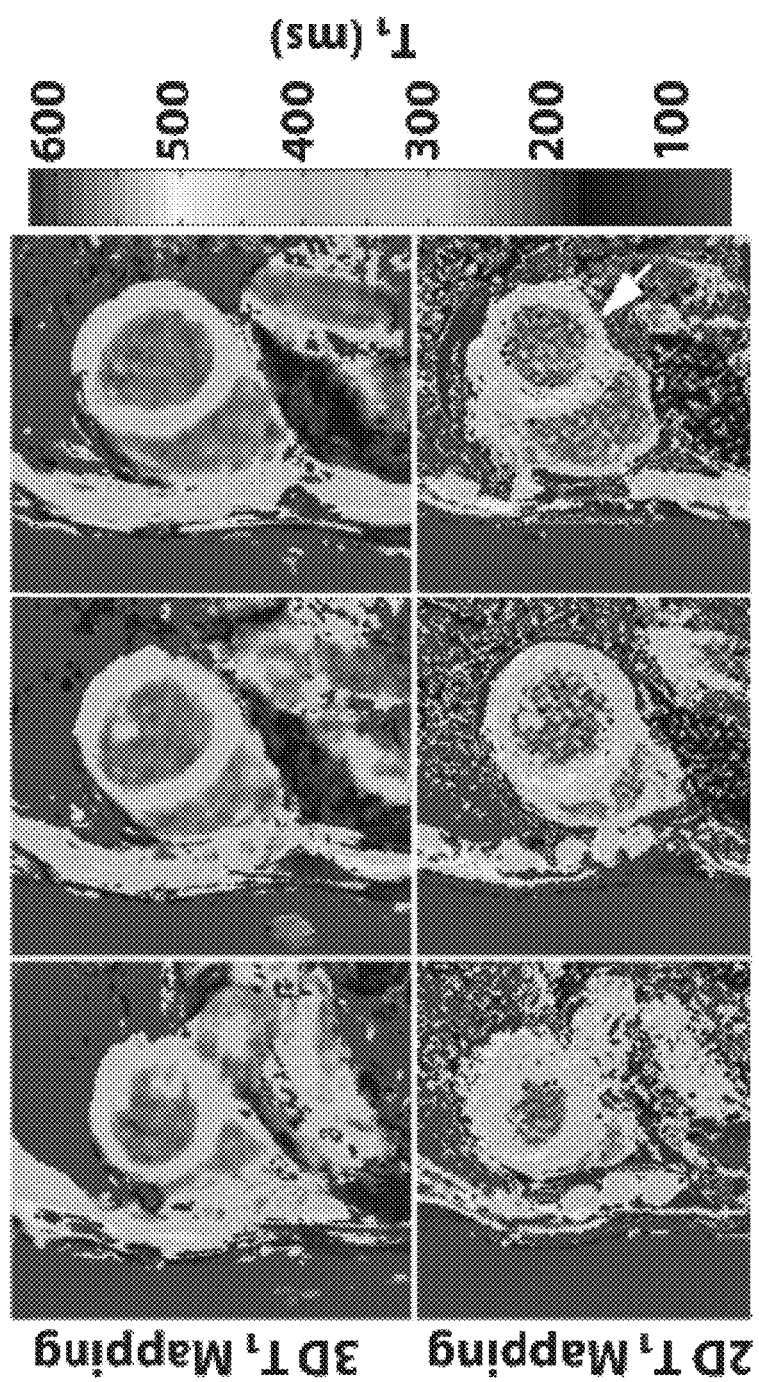
FIG. 7 is a series of exemplary of $T_1$ maps acquired in a healthy subject using a 2D multi-slice technique and 3D $T_1$ mapping technique in accordance with the present disclosure.

Multi-slice 2D MOLLI was performed using the following parameters: FOV=300×300 mm$^2$, in-plane resolution=1.7×2.1 mm$^2$, slice-thickness=10 mm, TR/TE=2.6 ms/1.03 ms, flip angle=40°, SENSE rate=2 and a total breath-held scan time (without rest periods in between breath-holds) of 2:40 minutes. FIG. 7 shows multiple slices of representative 3D $T_1$ maps acquired in a healthy subject in comparison to a multi-slice MOLLI sequence. The white arrow indicates artifacts at the epicardial border caused by motion between different $T_1$-weighted images.

Figure 8:
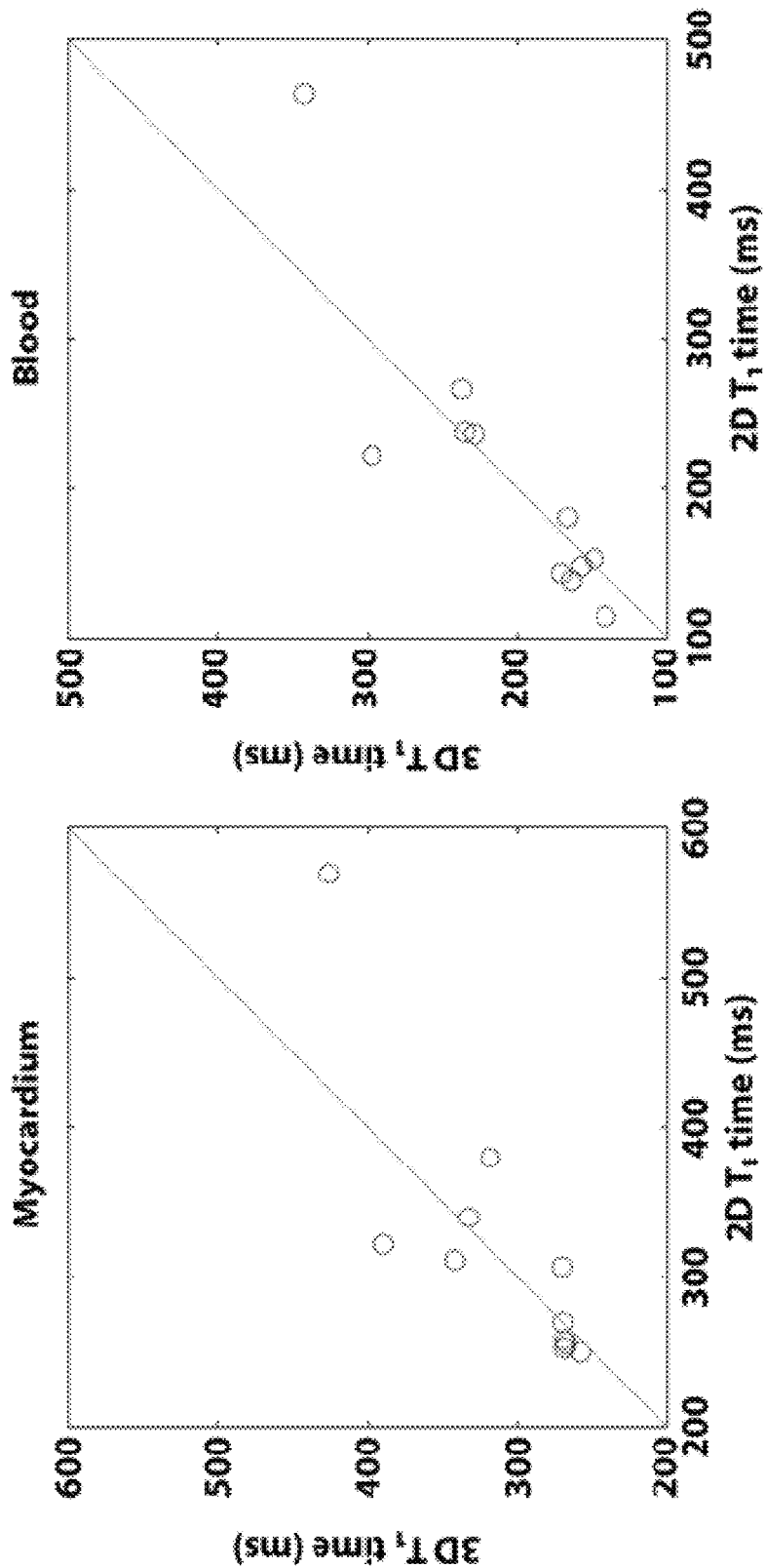
FIG. 8 is a plot comparing in-vivo $T_1$ times assessed in myocardium and blood pools using a 2D multi-slice technique and 3D $T_1$ mapping technique in accordance with the present disclosure.

Turning to FIG. 8, in-vivo $T_1$ times for myocardium tissue and left and right ventricle (RV) blood pools are summarized for all subjects, comparing the 3D sequence of the current invention and MOLLI performed in randomized order. It is observed that standard deviation within the blood pools was significantly decreased by using the 3D method compared to MOLLI, namely from 28±11 ms variation with MOLLI to 8.2±3.8 ms with the 3D method (P<0.05).

Figure 9:
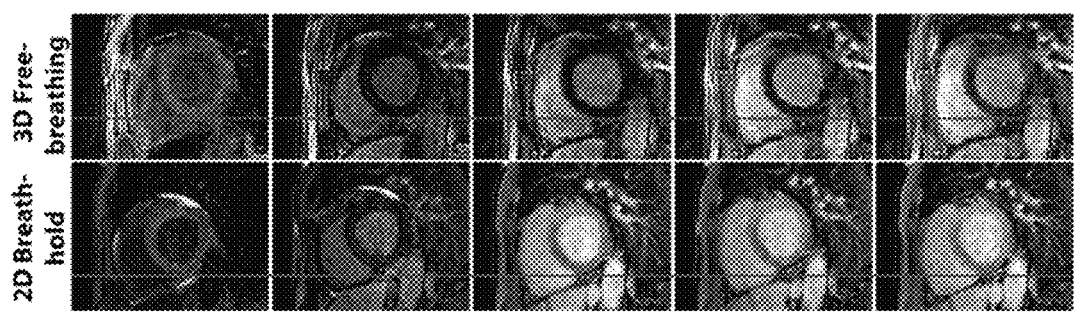
FIG. 9 is a series of images showing breathing effects for a series of $T_1$-weighted images of a healthy subject acquired using a breath-hold 2D multi-slice technique and free-breathing 3D $T_1$ mapping technique in accordance with the present disclosure.

FIG. 9 shows representative $T_1$ weighted images of an example slice of the 3D technique and MOLLI. Substantial respiratory-induced motion of the epicardial border with respect to the reference line can be observed in the MOLLI images, due to improper breath-holding. By contrast, the interleaved 3D acquisition is free of motion, as the myocardial border remains stationary among the images. The motion quantification, by tracking the LV center point showed displacements between 1.6±0.2 mm and 6.1±3.7 mm, with an average of 4.1±2 5 mm among all slices (standard deviation over the different subjects) for 2D $T_1$ mapping. For the 3D data set the offset was between 1.9±0.6 mm and 3.1±1 0 mm with a mean value of 2.5±0.6 mm. The scan time for the 3D sequence was 4:00 minutes on the average at low resolution, whereas the average scan time for the multi-slice MOLLI sequence was 9:45 minutes, including the rest periods between breath-holds.

Figure 10:
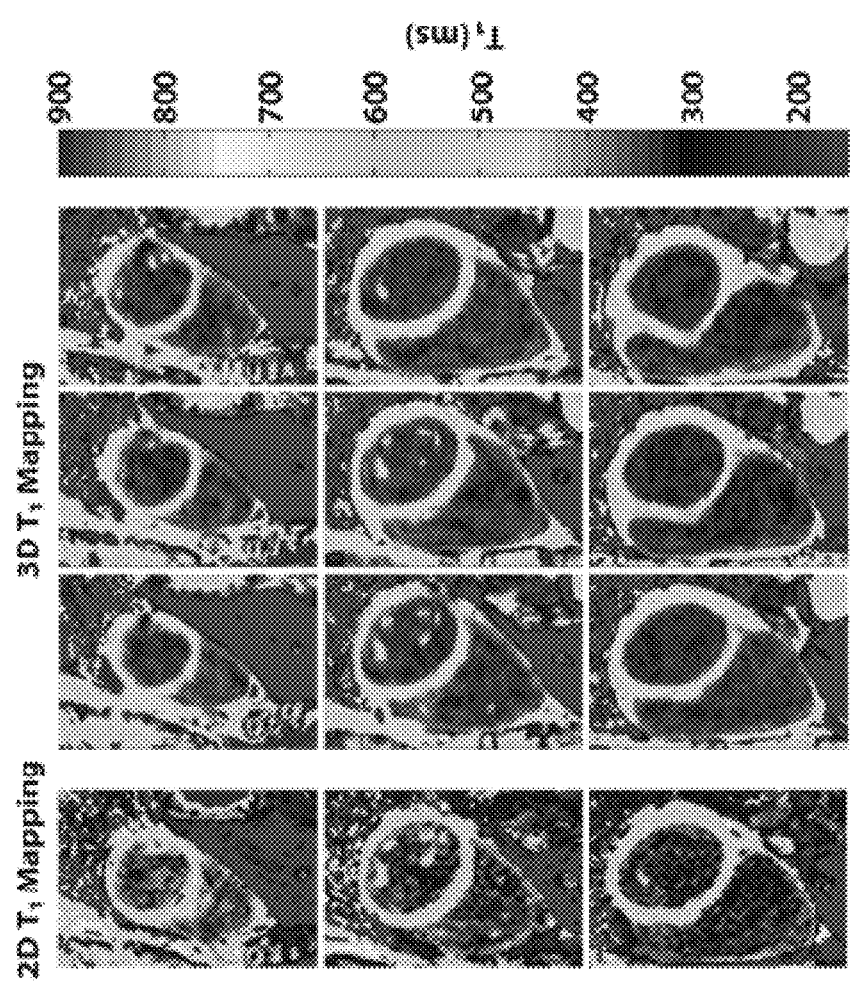
FIG. 10 is a series of images showing an example of representative slices in a healthy subject illustrating a low resolution using 2D multi-slice technique compared to a high resolution for 3D $T_1$ mapping technique in accordance with the present disclosure.

FIG. 10 shows representative slices of a high-resolution (1.7×1.7×4 mm$^3$) 3D $T_1$ map acquired in 9:26 min using the approach described herein. Visually improved image quality can be observed as compared to the 2D $T_1$ method, and includes a full LV coverage.

In summary, a novel 3D $T_1$ mapping approach has been described based on interleaved 3D acquisitions with a joint prospective-retrospective compressed-sensing motion correction, demonstrating the feasibility of free-breathing 3D myocardial $T_1$ mapping sequence for volumetric evaluation of cardiac tissue, such as LV diffuse fibrosis. The interleaved acquisition of multiple $T_1$-weighted inversion recovery images in combination ensures spatial alignment of images and enables the generation of 3D $T_1$ maps by performing a voxel-wise curve fit on a compressed sensing reconstruction of the acquired under-sampled data. The resulting 3D $T_1$ maps, acquired after contrast injection, allows whole heart coverage with reduced motion artifacts compared to 2D breath-hold multi-slice sequences.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for producing images of a subject using a magnetic resonance imaging (MRI) system, the method comprising:
   a) identifying a pre-determined point in a cardiac cycle of a subject;
   b) performing with a MRI system an inversion recovery (IR) pulse at a selected one of a plurality of time points within the cardiac cycle of the subject;
   c) sampling a segment of k-space with the MRI system at an inversion time from the IR pulse that is substantially coincident with the pre-determined point in the cardiac cycle;
   d) repeating steps b) and c) for a plurality of inversion times to achieve a plurality of T1-weighted contrasts by performing the IR pulse at a different one of the plurality of time points from the selected one of the plurality of time points until an IR pulse has been performed at all of the plurality of time points;
   e) performing step d) for each of a plurality of segments of k-space to generate datasets having T1-weighted contrasts determined by respective inversion times;
   f) reconstructing a set of three-dimensional (3D) spatially-aligned images using the datasets; and
   g) generating a T1 recovery map by combining the set of the 3D spatially-aligned images.

2. The method of claim 1 further comprising performing a navigator imaging acquisition to identify a pre-determined point in a respiratory cycle of the subject.

3. The method of claim 1, further comprising determining an occurrence of a motion during step c), comparing the occurrence of motion to a threshold, and if the motion was greater than the threshold, repeating step d) with an IR pulse at the selected one of the plurality of time points corresponding to the occurrence of the motion.

4. The method of claim 3, wherein repeating step d) with an IR pulse at the selected one of the plurality of time points corresponding to the occurrence of the motion is not performed if the segment of k-space acquired during the occurrence of the motion corresponds to a periphery of k-space.

5. The method of claim 1, wherein the plurality of inversion times in step d) are in range approximately between 100 and 600 milliseconds.

6. The method of claim 1, wherein step f) includes performing a compressed-sensing reconstruction technique.

7. The method of claim 1, wherein combining the set of spatially-aligned images is performed by a voxel-wise fit of a plurality of corresponding image intensities according to:

$$S(T_{inv};M_0,T_1)=M_0(1-2e^{-T_{inv}/T_1}) \qquad (1)$$

where S is an image intensity, $M_0$ is a spin density, $T_{inv}$ is an inversion time and $T_1$ is a longitudinal relaxation time.

8. A magnetic resonance imaging (MRI) system, comprising:
   a magnet system configured to generate a polarizing magnetic field about at least a portion of a subject arranged in the MRI system;

a magnetic gradient system including a plurality of magnetic gradient coils configured to apply at least one magnetic gradient field to the polarizing magnetic field;

a radio frequency (RF) system configured to apply an RF field to the subject and to receive magnetic resonance signals therefrom;

a computer system programmed to:

identify a pre-determined point in a cardiac cycle of a subject;

control the magnetic gradient system and the RF system according to a pulse sequence including:

i) perform an inversion recovery (IR) pulse at a selected one of a plurality of time points within the cardiac cycle of the subject and sample a segment of k-space at an inversion time from the IR pulse that is substantially coincident with the pre-determined point in the cardiac cycle;

ii) repeat i) for a plurality of inversion times to using IR pulses at different ones of the plurality of time points from the selected one of the plurality of time points until an IR pulse has been performed at all of the plurality of time points;

iii) repeat ii) for each of a plurality of segments of k-space to generate datasets having T1-weighted contrasts determined by respective inversion times;

iv) reconstruct a set of three-dimensional (3D) spatially-aligned images using the datasets; and v) generate a T1 recovery map by combining the set of the 3D spatially-aligned images.

9. The system of claim 8, the computer system further programmed to perform a navigator imaging acquisition to identify the pre-determined point in the cardiac cycle of the subject.

10. The system of claim 8, the computer system further programmed to determine an occurrence of a motion during step i), comparing the occurrence of motion to a threshold, and if the motion was greater than the threshold, repeating step ii) with an IR pulse at the selected one of the plurality of time points corresponding to the occurrence of the motion.

11. The system of claim 10, wherein repeating step ii) with an IR pulse at the selected one of the plurality of time points corresponding to the occurrence of the motion is not performed if the segment of k-space acquired during the occurrence of the motion corresponds to a periphery of k-space.

12. The system of claim 8, wherein the plurality of inversion times in step ii) are in range approximately between 100 and 600 milliseconds.

13. The system of claim 8, wherein the computer system is further programmed to perform a compressed-sensing reconstruction technique in step iv).

14. The system of claim 8, wherein combining the set of spatially-aligned images is performed by a voxel-wise fit of a plurality of corresponding image intensities according to:

$$S(T_{inv};M_0,T_1)=M_0(1-2e^{T_{inv}/T_1})$$

where S is an image intensity, $M_0$ is a spin density, $T_{inv}$ is an inversion time and $T_1$ is a longitudinal relaxation time.

* * * * *